United States Patent
Dubois et al.

(10) Patent No.: US 7,576,848 B2
(45) Date of Patent: *Aug. 18, 2009

(54) SYSTEM AND METHOD TO DECREASE PROBE SIZE FOR IMPROVED LASER ULTRASOUND DETECTION

(75) Inventors: Marc Dubois, Clifton Park, NY (US); Thomas E. Drake, Jr., Fort Worth, TX (US); Pavel Fomitchov, New York, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 392 days.

This patent is subject to a terminal disclaimer.

(21) Appl. No.: 11/018,994

(22) Filed: Dec. 21, 2004

(65) Prior Publication Data

US 2006/0132804 A1 Jun. 22, 2006

(51) Int. Cl.
*G01N 21/00* (2006.01)
(52) U.S. Cl. .................................... 356/237.1; 356/614
(58) Field of Classification Search .............. 356/237.1, 356/614
See application file for complete search history.

(56) References Cited

U.S. PATENT DOCUMENTS

| 4,581,939 | A | | 4/1986 | Takahashi |
| 4,659,224 | A | * | 4/1987 | Monchalin ................... 356/502 |
| 6,609,425 | B2 | | 8/2003 | Ogawa |
| 6,657,733 | B1 | * | 12/2003 | Drake, Jr. .................... 356/511 |
| 2005/0023434 | A1 | | 2/2005 | Yacoubian |
| 2006/0215174 | A1 | * | 9/2006 | Dubois et al. ................ 356/502 |

* cited by examiner

*Primary Examiner*—Roy M Punnoose
(74) *Attorney, Agent, or Firm*—Bracewell & Giuliani LLP

(57) ABSTRACT

The present invention provides a compact optical probe assembly that measures ultrasound in materials. The probe uses angle-terminated optical fiber to direct illumination laser light at the surface of a remote target. Ultrasonic displacements at the surface scatter the illumination laser light. Angle-terminated optical fibers collect phase modulated light and direct the phase modulated light to an optical processor to produce a signal representative of the ultrasonic surface displacements. The probe may also incorporate angle-terminated optical fibers to direct generation laser light to the surface of a remote target to generate ultrasonic surface displacements. Optional shared beam forming element(s) may optically act on the illumination laser and collected phase modulated light.

11 Claims, 11 Drawing Sheets

SYSTEM AND METHOD TO DECREASE PROBE SIZE FOR IMPROVED LASER ULTRASOUND DETECTION

CROSS-REFERENCE TO RELATED APPLICATION

This application is related to and is incorporated herein by reference in its entirety to U.S. patent application Ser. No. 10/142,178 entitled "System and Method for Controlling Wafer Temperature", filed on May 9, 2002, which is a continuation-in-part of and claims priority to Ser. No. 09/416,399 entitled Method and Apparatus for Detecting Ultrasonic Surface Displacements Using Post Collection Optical Amplification" to Thomas E. Drake filed on Oct. 12, 1999, which claims priority to U.S. Provisional Patent Application No. 60/091,229 filed on Jun. 30, 1998.

TECHNICAL FIELD OF THE INVENTION

The present invention relates generally to the generation and detection of ultrasound in materials using lasers, and more particularly, to a system and method that significantly reduces the size of probe for laser ultrasound detection.

BACKGROUND OF THE INVENTION

In recent years, the use of advanced composite structures has experienced tremendous growth in the aerospace, automotive, and many other commercial industries. While composite materials offer significant improvements in performance, they require strict quality control procedures in the manufacturing processes. Specifically, non-destructive evaluation (NDE) methods must assess the structural integrity of composite materials. Conventional NDE methods are slow, labor-intensive, and costly. As a result, testing procedures adversely increase the manufacturing costs associated with composite structures.

Various methods and apparatuses have been proposed to assess the structural integrity of composite structures. One method generates and detects ultrasound using lasers. A pulsed laser beam generates ultrasound on a work piece, while a second laser beam illuminates the work piece. Surface displacements generated by the generation laser modulate the illumination laser beam, and the modulated laser energy is collected with collection optics. The modulated light is processed to extract useful information about the structural integrity of the target.

One advantage provided by such a laser ultrasound inspection is the ability to perform ultrasonic measurements without mechanically coupling or contacting the target to be inspected. Additionally, laser ultrasound may provide low sensitivity to the orientation of the sample relative to the illuminating laser beam. These abilities make laser ultrasound highly useful in the inspection of parts.

Laser ultrasound requires a line of sight for the laser to carry out the measurement. However due to the complex shapes often inspected, it is difficult to realize a line of sight from the laser source to the sample being inspected. One solution brings optical fibers near the area to be inspected. In such a case, multiple optical fibers transport multiple lasers to generate laser ultrasound and illuminate the ultrasonic displacements at the target. The fibers also serve to collect phase modulated light scattered at the target. In this arrangement, different optical setups may be used for each optical fiber. These different optical setups can cause the laser ultrasound probe to become cumbersome. Additionally, system optics associated with ultrasound generation, detection, and collection in the path of one another may decrease the optical efficiency of the system while increasing the size and complexity.

One solution to uses separate devices for ultrasound generation, illumination and collection. However, the use of multiple devices increases the time to perform inspections, requires multiple operators working together to take measurements, requires more powerful and expensive lasers, and results in lower measurement accuracy.

When direct line of sight is not available optical fibers can be used to bring the laser light at a condition from which the inspection can be carried out. Usually this requires the use of multiple optical fibers. The use of the multiple optical fibers often requires different optical setups for each optical fiber. Multiple optical fiber probes historically have made the remote access laser ultrasound head bulky and not optically efficient as their optics interferes with one another. A decrease in optical efficiency very often compensated for by increasing the size of the collection optics for the power associated with the lasers. However this solution makes the laser ultrasound probe larger than during access to confined spaces more difficult.

Fiber optics laser ultrasound heads have been designed for the purpose of remote access laser ultrasound inspection using individual optics for each optical fiber. These probes are bulky and require high-powered detection in order to compensate for the low collection efficiency. These probes can be made less bulky by using a single fiber for the laser illumination and light collection. However, this configuration tends to produce high parasitic noise due to back reflections. Another alternative solution utilizes piezoelectric transducers to generate ultrasound. This solution is not always attractive as this requires mechanical contact with the inspection area and a very high degree of control associated with the orientation of the transducer relative to the inspection area (i.e. the transducer must be normal to the inspected surface). These requirements make inspection difficult, slow, and expensive. Additionally, the use of transducers requires the use of wires physically coupled to the transducer for power, etc. In some cases, measurements must be performed in flammable environments where no wire may be brought near the inspection area. For these reasons, optical fibers are more desirable. Therefore, a need exists for a more effective system and method to perform laser ultrasonic testing in confined spaces or on complex work pieces.

Therefore, a need exists for a more effective system and method to perform laser ultrasonic testing in confined spaces or on complex work pieces.

SUMMARY OF THE INVENTION

The present invention provides an apparatus and method to detect ultrasonic surface displacements on a remote target that substantially eliminates or reduces disadvantages and problems associated with previously developed systems and methods. More specifically, the present invention provides a compact laser ultrasonic probe to detect ultrasonic surface displacements on a remote target using laser ultrasound that incorporates angle-terminated optical fibers.

Terminating the optical fiber at specific angles allows the optical axis of the individual optical fibers to be adjusted relative to the longitudinal axis of the optical fiber. Multiple angle-terminated optical fibers can be incorporated in a compact optical probe in such a manner that the fields of view of the optical fibers completely or nearly completely overlap. An ultrasonic source produces ultrasonic displacements at the surface of the remote target such as a composite material under test. One embodiment employs a generation laser to generate an ultrasonic generation laser beam that is provided to the remote target through the optical fibers. The laser beam is directed by the angle-terminated optical fibers of the compact optical prob. The generation laser produces ultrasonic displacements at the surface of the remote target. Other ultrasound generation sources known by those skilled in the art may be employed.

An illumination laser source generates an illumination laser beam operable to detect ultrasonic displacements at the surface. The illumination laser beams aimed at the surface of the target with the compact optical probe made from angle-terminated optical fiber. The illumination laser interacts with the ultrasonic displacements to produce phase-modulated light. This phase-modulated light, scattered or reflected at the surface of the target is collected for optical processing by a third angle-terminated optical fiber. Additionally, the probe may employ an optical lens to focus the light entering and exiting the probe. An interferometer or other optical like device known to those skilled in the art then processes the collected phase modulated light to generate an output signal containing data representative of the ultrasonic surface displacements on the surface of the remote target. This signal may be further processed to reveal or generate an image of the structure of the remote target.

Another embodiment of the present invention provides a method for performing ultrasonic measurements for generating and measuring ultrasonic displacements on the surface of the target. This method involves generating the ultrasonic displacements at the surface of the target or work piece. This may be done using a generation laser beam provided via a compact optical probe or other means known to those skilled in the art. Next an illumination laser beam illuminates the ultrasonic displacements at the surface of the work piece. This illumination laser beam may also be provided via the same compact optical probe. The illumination laser beam is scattered by the ultrasonic surface displacements to produce phase modulated light which may then be collected by the compact optical probe. The compact optical probe may include angle-terminated optical fibers for the illumination laser beam, generation laser beam, and to collect phase modulated light. The phase modulated light may then be processed to obtain data representative of ultrasonic surface displacements at the target and thereby yield information on the internal structure of the remote target. The illumination by the angle-terminated optical fiber associated with the generation laser beam and illumination laser beam may overlap increasing the efficiency for ultrasound generation and detection.

A laser ultrasound inspection system incorporating a compact optical probe made with angle-terminated optical fiber can be made. This laser ultrasound inspection system includes a generation laser source, an illumination laser source, a bundle of angle-terminated optical fibers to direct the generation laser beam, illumination laser beam in overlapping fields on the surface of a work piece to be inspected, collection optical fiber(s), and an optical and data processing system to obtain data representative of the internal structure of the remote target from the collected, phase modulated light. This inspection system results in the ability to detect defects within materials, such as composite material, more easily and quickly.

The compact optical probe of the present invention provides significant operational improvements over prior solutions in performing inspections of materials. Other features and advantages of the present invention will become apparent from the following detailed description of the invention made with reference to the accompanying drawings.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE INVENTION

Embodiments of the present invention are illustrated in the FIGs, like numerals being used for like and corresponding parts of the various drawings.

The present invention provides the ability to use the same optics for generation, detection and collection of laser light associated with a laser ultrasound inspection system. No additional optics is required by terminating the optical fibers at pre-determined angles so that the field of view or optical spots of each optical fiber overlap. The elimination of additional optics can reduce the size and complexity of the laser ultrasound probe while increasing it's the probes flexibility and versatility. Additionally, because the generation, collection and detection optical field overlap the overall efficiency for ultrasound generation and detection is increased.

Figure 1:
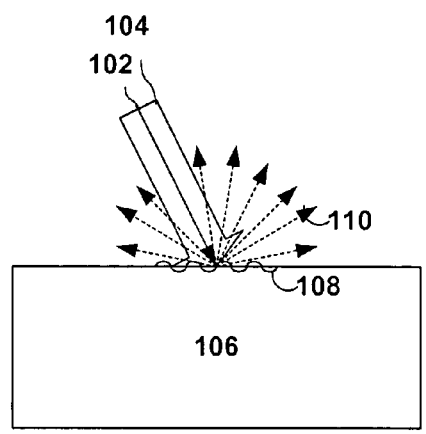
FIG. 1 illustrates the use of generation laser beam and a detection laser beam to generate and detect laser ultrasound.

FIG. 1 depicts two incoming laser beams that generate and detect laser ultrasonic displacements. Laser beam 102 generates ultrasound while illumination laser beam 104 detects the ultrasound at a remote target 106, such as a composite material under test. As shown, these lasers may be coaxially applied to remote target 106. Generation laser beam 102 causes thermo-elastic expansion in target 106 that results in the formation of ultrasonic deformations 108. Deformations 108 modulate, scatter and reflect illumination laser beam 104 to produce phase-modulated light 110 directed away from target 106 which is collected and processed to obtain information of the internal structure of remote target 106.

Figure 2:
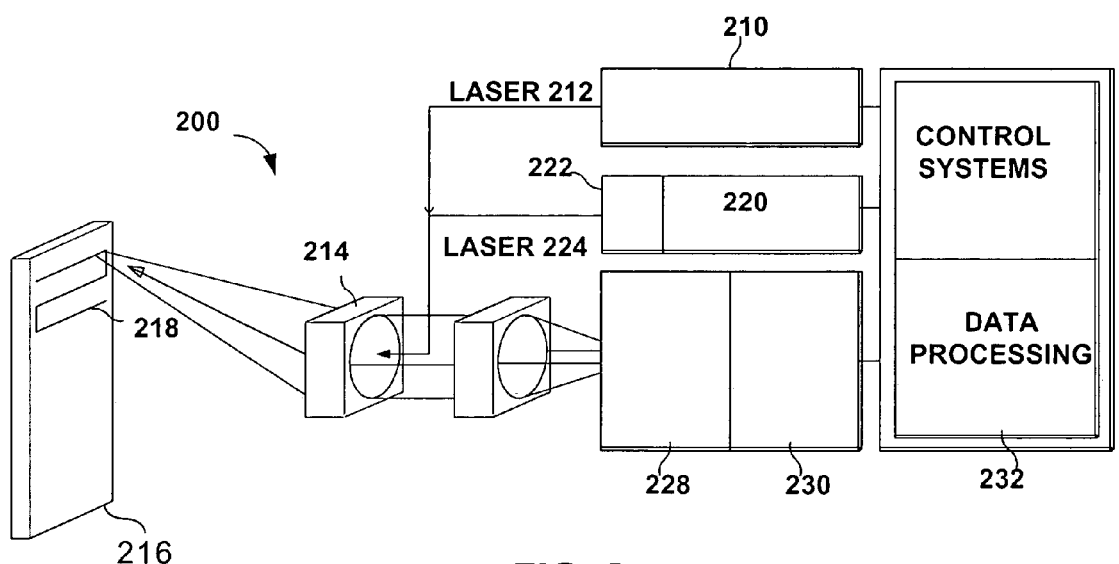
FIG. 2 provides a block diagram to show the basic components of laser ultrasound system.

FIG. 2 provides a block diagram with the basic components for performing ultrasonic laser testing. Generation laser 210 produces laser beam 212 which optical assembly 214 directs to target 216. As shown, optical assembly 214 includes a scanner or other like mechanism that moves laser beam 212 along a scan or test plan 218. Generation laser 210 produces a ultrasonic wave 108 within target 216.

The ultrasonic wave is the result of thermo-elastic expansion of the composite material as the material absorbs the generation laser beam. Composite material 216 readily absorbs generation laser beam 212 without ablating or breaking down.

Higher powered generation lasers are not necessarily preferred to overcome SNR issues as these can result in ablation. In other embodiments, depending on the material being tested, some ablation may be acceptable in order to increase the SNR of the detected signal. Generation laser beam 212 has appropriate pulse duration to induce ultrasonic surface deformations. For example, a transverse-excited atmospheric (TEA) $CO_2$ laser can produce a 10.6 micron wavelength beam for a 100 nanosecond pulse. The power of the laser must be sufficient to deliver, for example, a 0.25 joule pulse to the target, which may require a 100 watt laser operating at a 400 Hz pulse repetition rate. Generation laser beam 212 absorbs as heat into the target surface thereby causing thermo-elastic expansion without ablation.

Illumination laser 220 operation pulsed mode or continuous wave mode as to not induce ultrasonic displacements. For example, an Nd:YAG laser can be used. The power of this laser must be sufficient to deliver, for example, a 100 milli-joule, 100 micro-second pulse, which may require a one kilo-watt laser.

Illumination laser 220 generates detection laser beam 222. Illumination laser 220 includes or optically couples to filtering mechanism 224 to remove noise from detection laser beam 224. Optical assembly 214 directs illumination laser beam 224 to the surface of composite material 216 which scatters and/or reflects detection laser beam 224. Resultant phase modulated light is collected by collection optics 226. As shown here, scattered and/or reflected illumination laser travels back through optical assembly 214. Optional optical processor 228 and interferometer 230 process the phase modulated light to produce a signal containing information representative of the ultrasonic displacements at the surface of composite material 216. Data processing and control system 232 coordinate operation of the laser ultrasound system components.

Data processing and control system 232 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on operational instructions stored in memory. The memory may be a single memory device or a plurality of memory devices. Such a memory device may be a read-only memory, random access memory, volatile memory, non-volatile memory, static memory, dynamic memory, flash memory, cache memory, and/or any device that stores digital information. The memory stores, and data processing and control system 232 executes, operational instructions corresponding to at least some of the steps and/or functions as will be illustrated in FIG. 8.

Figure 3:
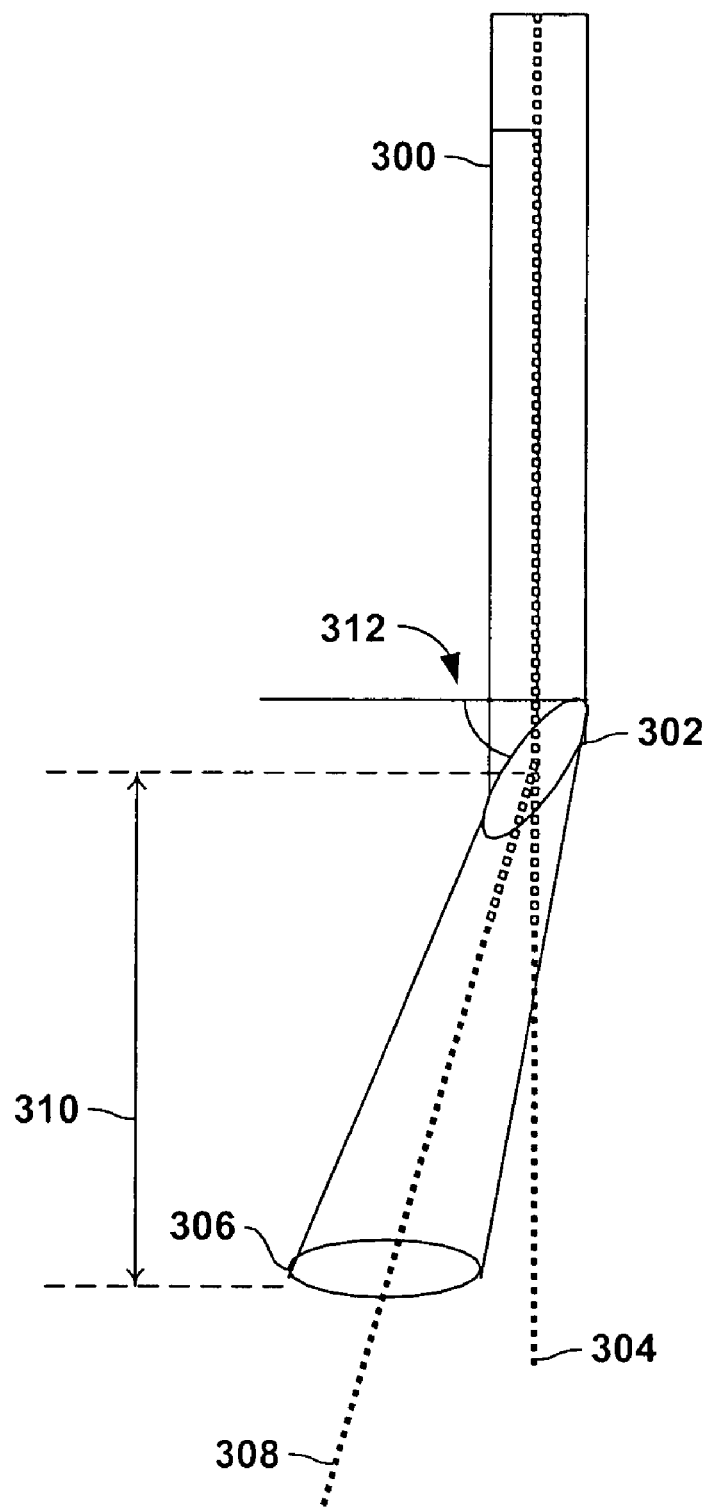
FIG. 3 illustrates the use of angle-terminated optical fiber to direct laser light or create a collection axis for reflected light.

FIG. 3 illustrates the use of angle-terminated optical fiber 300 to direct laser light or collect along an optical axis for reflected light. Optical fiber 300, with longitudinal physical axis 304, is terminated at a specified angle 312, cut and optically polished to create facet 302. Facet 302, acting as an optical wedge to provide optical axis 308. Generation or illumination laser light can be projected from such a fiber along optical axis 308. Alternately, phase modulated light can be collected along optical axis 308. Field of view 306 is created at distance 310 from optical fiber 300. Termination angle 312 and distance 310 can be adjusted to change the location and size of field of view 306. Additionally, the optical fiber 300 may terminate in a lens or flat surface. The flat surface is applicable to fibers used for illumination or collection by a central optical fiber within a bundle of fibers.

Figure 4A:
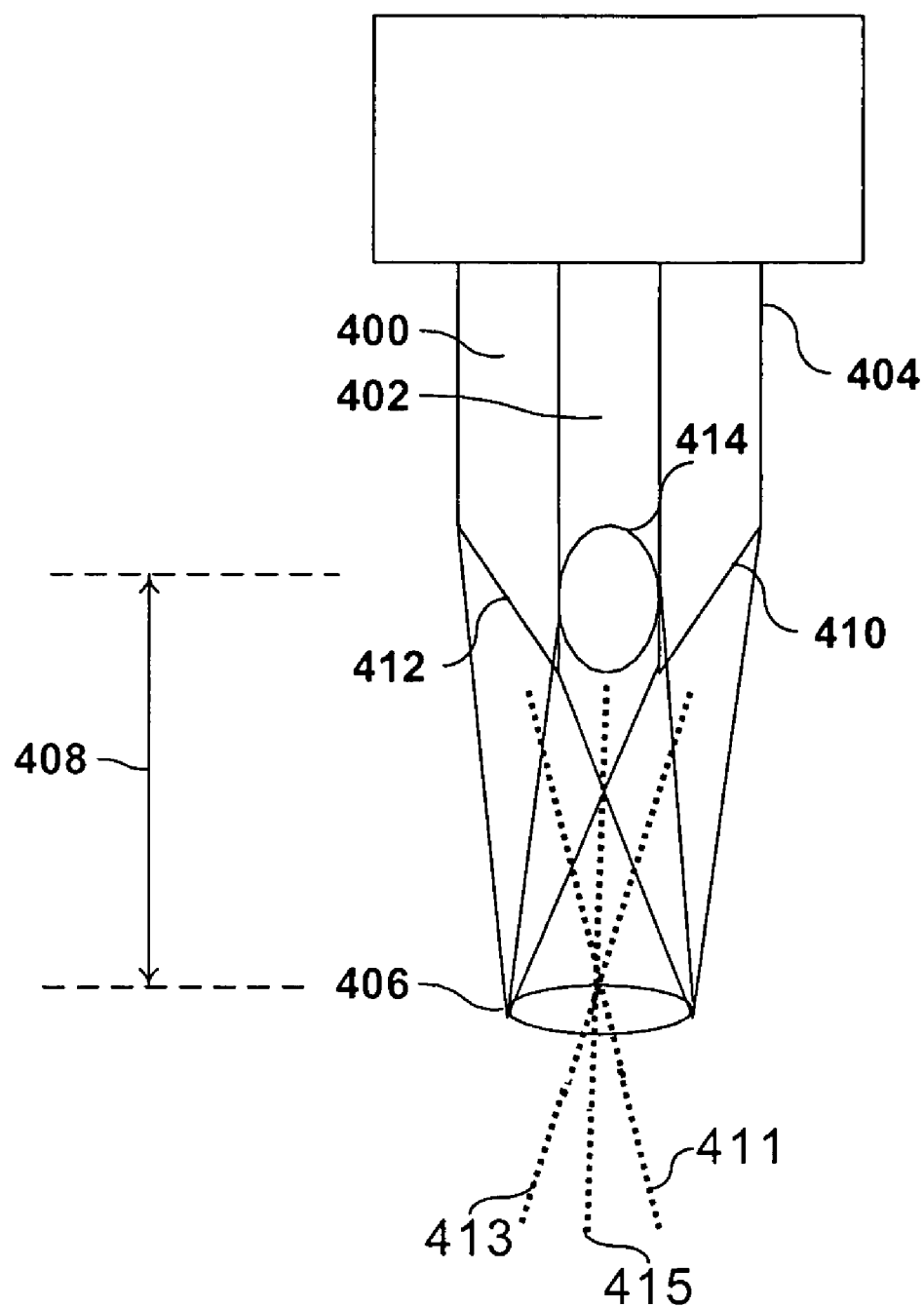
FIGS. 4A, 4B, and 4C illustrate the use of three angle-terminated optical fibers to create a compact optical probe incorporating a laser generation probe, an illumination laser probe, and a collection optics probe with a common field of view.

FIG. 4A illustrates the use of three angle-terminated optical fibers to create a compact optical probe that transport a laser generation beam, an illumination laser beam, and scattered laser modulated light with a number of optical fibers having a common field of view. Optical fibers 402, 404 and 406 bundle together to form a compact probe assembly 400. Optical fiber 402 provides an optical channel to transport the generation laser beam 102. Optical fiber 404 provides an optical channel to transport the illumination laser beam 104. Optical fiber 406 provides and optical channel to transport collected phase-modulated light 110. Optical fibers 400, 402 and 404 are terminated at specific angles, with facets 410, 412, and 414 to create a common field of view 406 at distance 408.

Figure 4B:
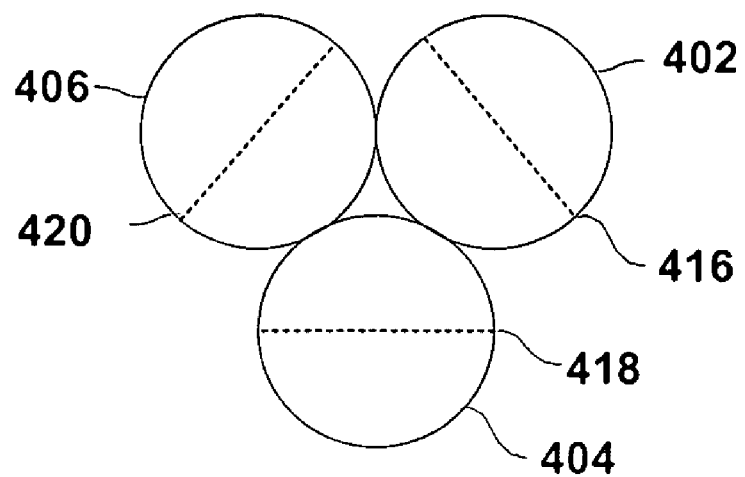

FIG. 4B illustrates an end view of the three optical fibers of 402, 404, and 406 within compact optical probe 400. Optical fibers 402, 404 and 406 are terminated at specific angles to form facets 410, 412, and 414 with optical axes 411, 413, and 415 respectively. Dotted lines 416, 418 and 420 indicate the orientation of the polished facet of each angle-terminated fiber.

Figure 4C:
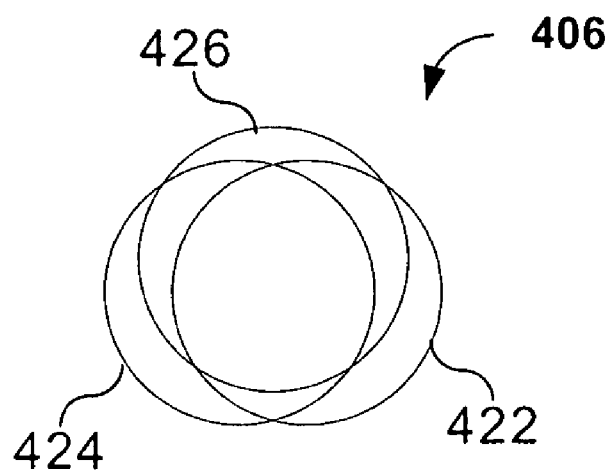

FIG. 4C illustrates the overlapping field of view 406. Fields of views 422, 424, and 426 of each of the three angle-terminated fibers 402, 404, and 406 overlap and may share a common focal point. By overlapping the field of view of each optical fiber, the optical efficiency of the probe can be increased.

Figure 5:
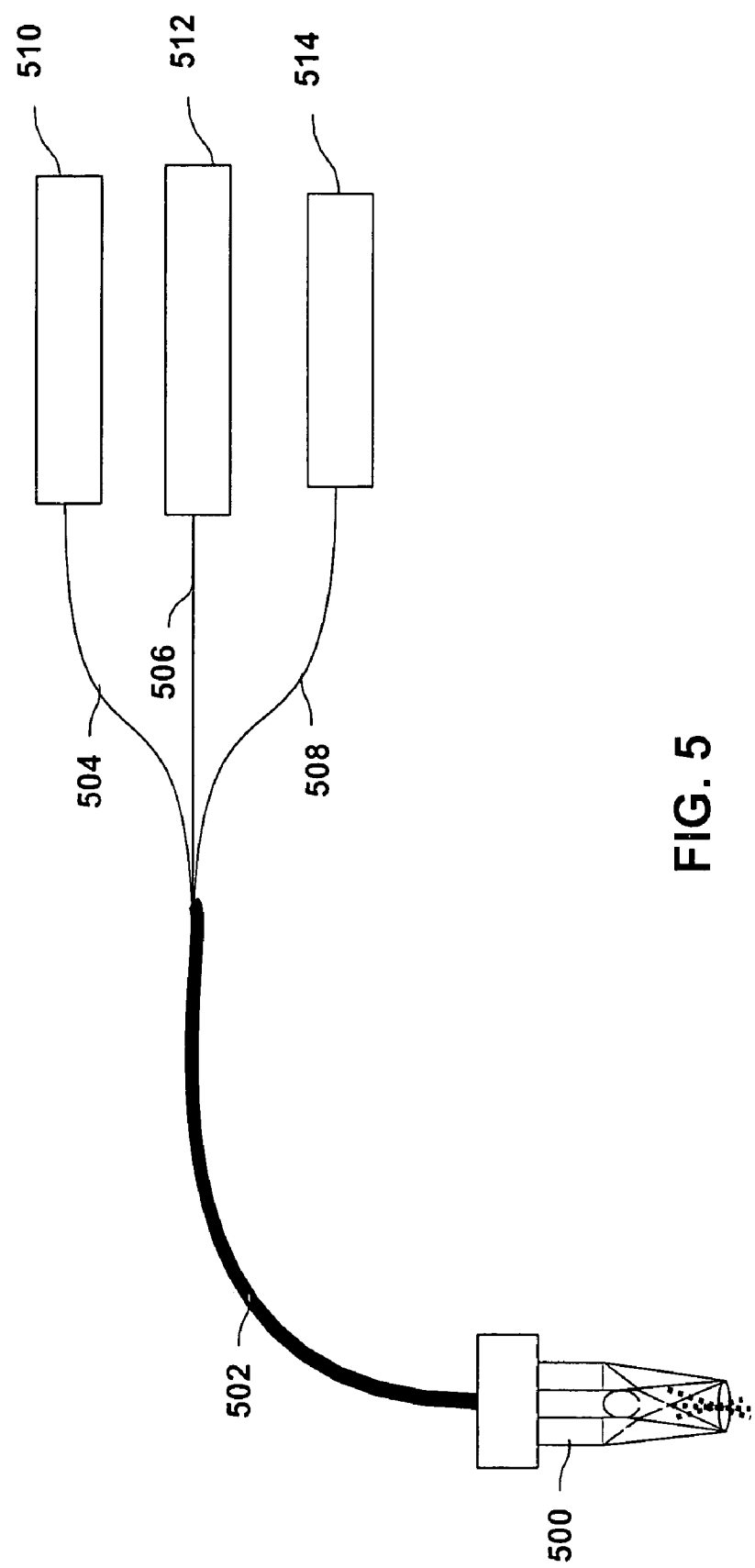
FIG. 5 provides a diagram to show a compact optical probe incorporating a laser generation probe, an illumination laser probe, and a collection optics probe incorporated in a laser ultrasound system.

FIG. 5 provides a block diagram of a portion of a laser ultrasonic testing system having a compact optical probe 500 that transports a laser generation beam, an illumination laser beam, and collected scattered phase-modulated light with fiber bundle 502. Fiber bundle 502 includes optical fibers 504, 506 and 508. Fibers 504, 506, and 508 optically couple probe 500 to a laser ultrasound inspection system. Optical fiber 504 may optically couple to generation laser source 510. Optical fiber 506 may optically couple to illumination or detection laser source 512. Optical fiber 508 may optically couple to an optical processor 514, such as an interferometer.

Figure 6:
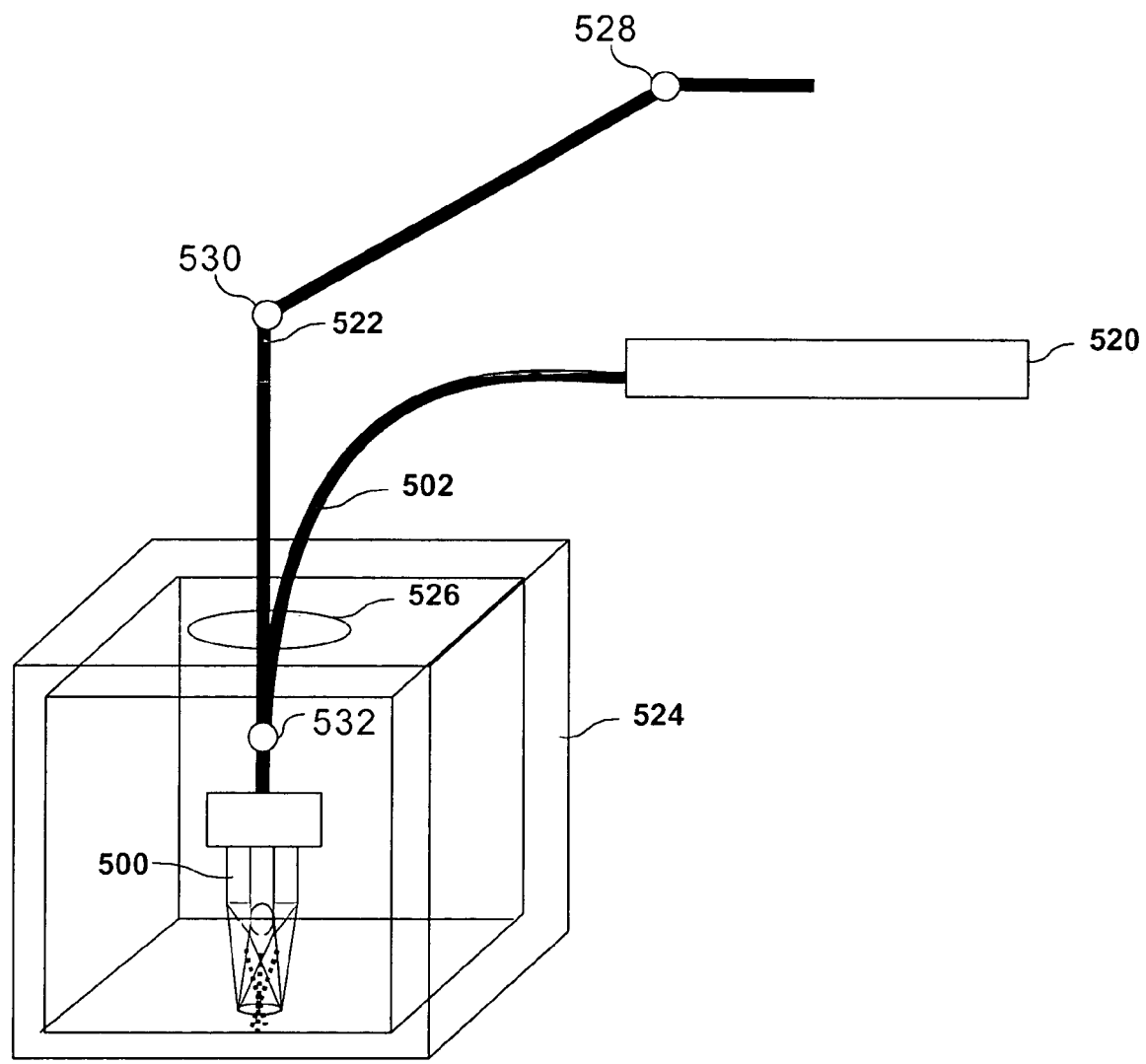
FIG. 6 illustrates the use of a compact optical probe incorporating a laser generation probe, an illumination laser probe, and a collection optics probe incorporated in a laser ultrasound system to inspect a surface with limited physical access.

FIG. 6 depicts the use of compact optical probe 500 to transport a laser generation beam, an illumination or detection laser beam, and collected phase modulated light. This allows the laser ultrasound system to inspect complex surfaces or surfaces in areas having limited physical access. Compact optical probe 500 couples to laser ultrasound system 520 via fiber bundle 502. This particular embodiment shows compact optical probe 500 mechanically couples to mechanical arm 522 to inspect the interior surfaces of object 524. In this instance compact optical probe 500 enters through access port 526. Mechanical arm 522 may be articulated at joints 528, 530, and 532 in order to reposition compact optical probe 500 in the X, Y, and Z direction. These multiple degrees of freedom provided by the articulated joints and flexibility of optical bundles 502 allow compact optical probes to be used to inspect any interior or exterior surface of object 524.

Figure 7A:
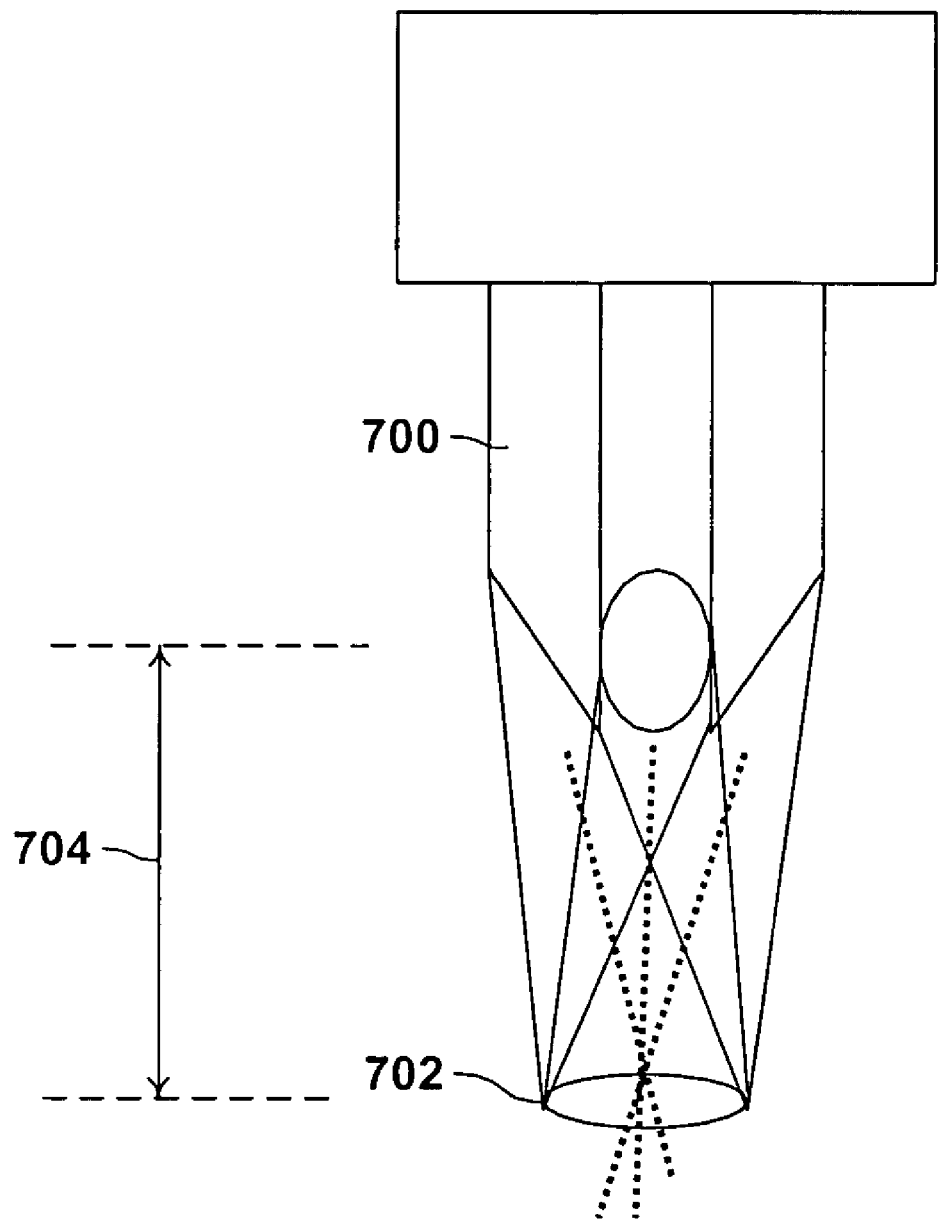
FIGS. 7A, 7B, 7C, 7D and 7E illustrate the use of seven angle-terminated optical fibers to create a compact optical probe incorporating an illumination laser probe and a collection optics probe with a common focal point.

FIG. 7A depicts compact optical probe 700 which in this embodiment uses seven angle-terminated optical fibers. Compact optical probe 700 transports the illumination laser beam 102 and a collected phase modulated light 110 with angle terminated fibers having a common field of view. The generation laser may be transported by the fiber bundle as well.

Figure 7B:
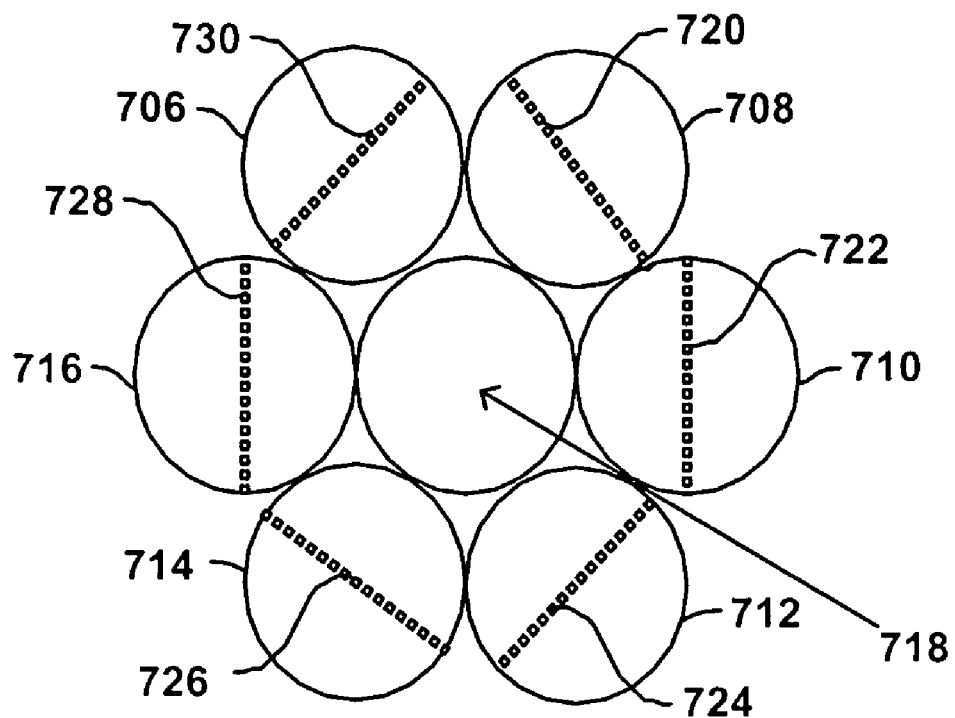
Figure 7C:
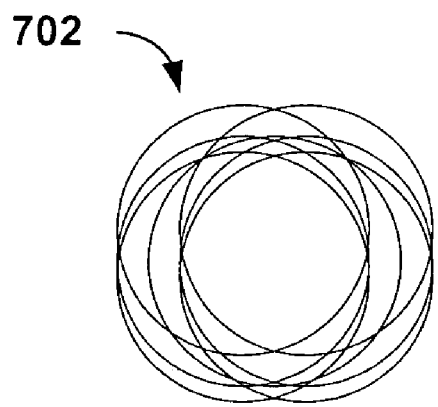

FIG. 7B illustrates an end view of seven optical fibers of compact optical probe 700 illustrated in FIG. 7A that form a hexagon. Six angle-terminated collection optical fibers 706, 708, 710, 712, 714, and 716 surround central illumination fiber 718. Dotted lines 720, 722, 724, 726, 728 and 730 indicate the orientation of the polished facet of each angle-terminated fiber. FIG. 7C illustrates an overhead view of the intersecting fields of view 702 that principally cover the same area The fields of view of each of the seven angle-terminated fibers are as concentric and overlap to a great extent.

Figure 7D:
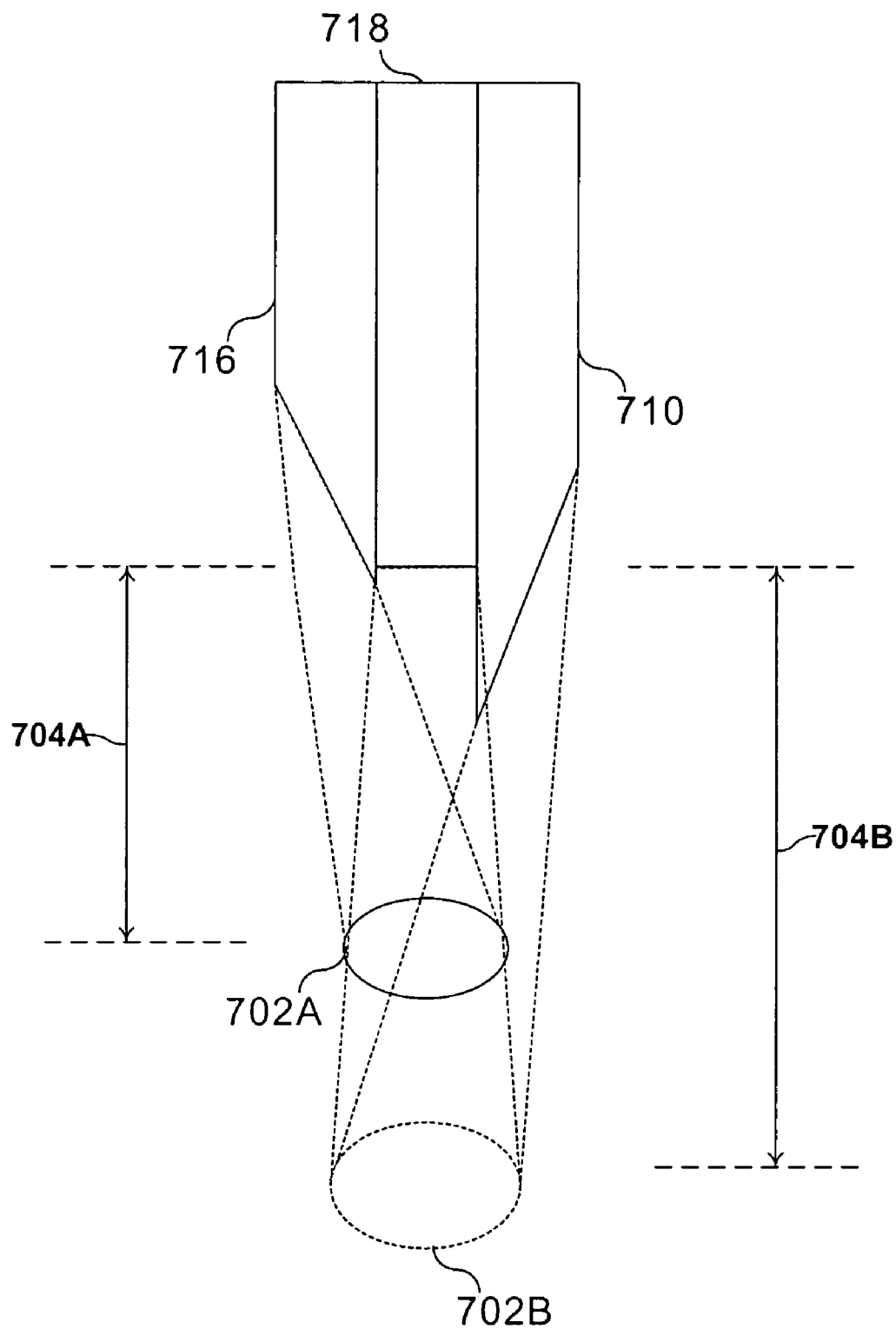

In FIG. 7D the orientation of the polished facets of each angle-terminated fiber vary. The angle-terminated collection optical fibers may have facets or lenses that differ. Optical fiber 716 and optical fiber 710 have different facets that allow their spot illumination or field of view, 702A and 702B respectively, to intersect the field of view of central fiber 718 at different distances, 704A and 704B, from the optical probe 700. Thus each facet may be created to maximize the optical efficiency for a particular application.

Figure 7E:
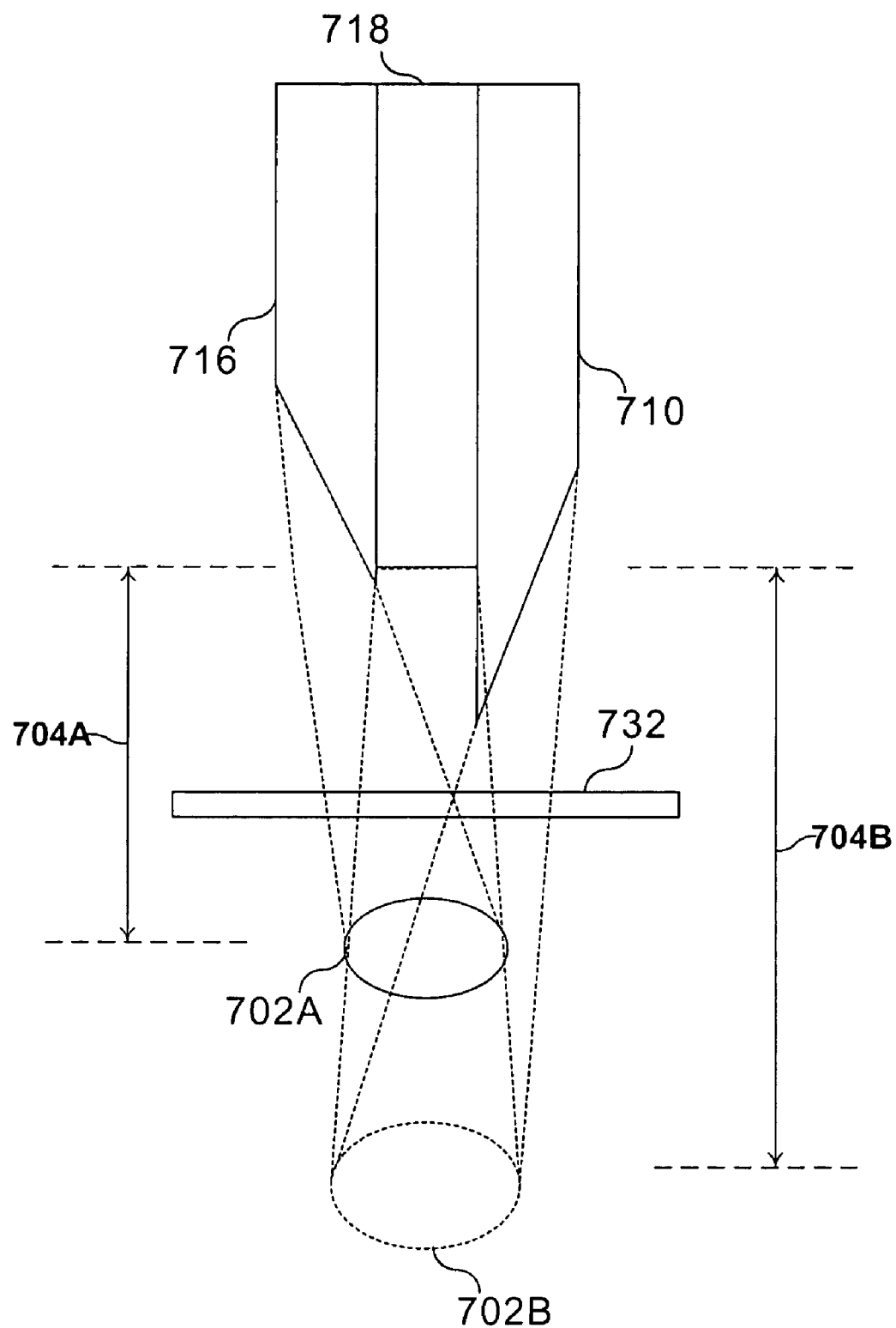

FIG. 7E depicts that a beam forming element, 732, such as a lens, grating or other like device known to those skilled in the art, may be placed between the optical fibers and field of view.

For detection or illumination central optical fiber 718 which is not angle terminated may be at the center of the optical fiber bundle forming a hexagon. The surrounding fibers are angle-terminated and each individual angle or facet may be chosen so that the spot seen by each fiber overlaps the illuminated field of view of the central fiber at a particular distance for specialized applications. This may allow the distance between the optical probe and the remote target to vary. Alternatively each angle-terminated fiber may overlap at one point from the central fiber. Several configurations are possible when optical fiber positions in the head and tip angles or facets are calculated to maximum optical efficiency for each particular application. Additionally these outer fibers may perform various functions. For example one collection fiber could be replaced and used as a generation fiber that is angle-terminated. Other configurations containing even more fibers can also be conceived. Such configurations might contain fibers having several different termination angles in order to make the field of view overlap as much as possible. It is also possible that the fibers be terminated by a curved surface instead of a flat angled surface.

Figure 8:
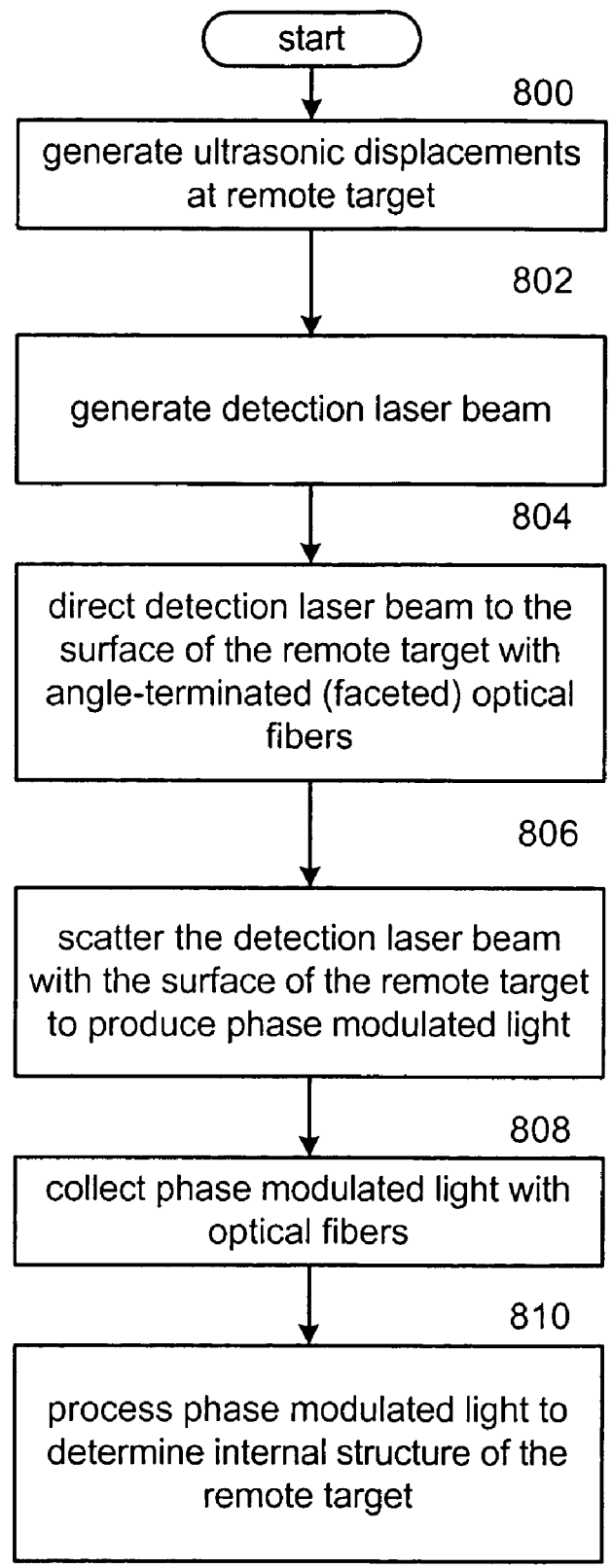
FIG. 8 is a logic flow diagram that depicts a method of detecting laser ultrasound with an optical probe in accordance with one embodiment of the present invention.

FIG. 8 is a logic flow diagram that depicts a method of detecting laser ultrasound with a detection laser delivered to the surface of a remote target with an optical probe as described above in accordance with one embodiment of the present invention. Ultrasonic surface displacements are generated at a surface of the remote target in step 800. In step 802, a detection laser beam is generated for delivery to the surface of a remote target in step 804 using an optical probe as described in FIGS. 1-7D. In step 806, the remote target then scatters the detection laser beam with ultrasonic surface displacements at its surface to produce phase-modulated light. The phase-modulated light is collected at step 808 with optical fibers using an optical probe as described in FIGS. 1-7D. Then the phase modulated light is processed in step 810 to obtain data representative of the ultrasonic surface displacements at the surface.

In operation the present invention allows laser ultrasonic test equipment to be used in a wider range of environments while testing more complex surfaces or surfaces within limited access areas. The present invention also allows existing laser ultrasound equipment to be modified to test more complex surfaces or surfaces within limited access areas without replacing the existing detection laser, an expensive component in the laser ultrasound system.

As one of average skill in the art will appreciate, the term "substantially" or "approximately", as may be used herein, provides an industry-accepted tolerance to its corresponding term. Such an industry-accepted tolerance ranges from less than one percent to twenty percent and corresponds to, but is not limited to, component values, integrated circuit process variations, temperature variations, rise and fall times, and/or thermal noise. As one of average skill in the art will further appreciate, the term "operably coupled", as may be used herein, includes direct coupling and indirect coupling via another component, element, circuit, or module where, for indirect coupling, the intervening component, element, circuit, or module does not modify the information of a signal but may adjust its current level, voltage level, and/or power level. As one of average skill in the art will also appreciate, inferred coupling (i.e., where one element is coupled to another element by inference) includes direct and indirect coupling between two elements in the same manner as "operably coupled". As one of average skill in the art will further appreciate, the term "compares favorably", as may be used herein, indicates that a comparison between two or more elements, items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

Although the present invention has been described in detail, it should be understood that various changes, substitutions and alterations can be made hereto without departing from the spirit and scope of the invention as defined by the appended claims.

What is claimed is:

1. A method for making ultrasonic measurements on a remote target comprising:
   generating ultrasonic surface displacements at a surface of the remote target;
   generating an illumination laser beam;
   directing the illumination laser beam to the surface of the remote target with at least one optical fiber;
   scattering the illumination laser beam with the ultrasonic surface displacements to produce phase-modulated light;
   collecting the phase-modulated light with at least one additional optical fiber wherein the at least one optical fiber terminates with an angled or curved surface and wherein a field of view of the optical fibers substantially overlap;
   processing the phase-modulated light to obtain data representative of the ultrasonic surface displacements at the surface; and
   rendering the ultrasonic measurements on the remote target based on the data representative of the ultrasonic surface displacements.

2. The method of claim 1, wherein generating ultrasonic surface displacements further comprises generating a generation laser beam.

3. The method of claim 2, further comprising directing the generation beam to the surface of the remote target with at least one optical fiber.

4. The method of claim 1, further comprising optically manipulating the illuminator laser beam and phase modulated light with a shared beam forming element.

5. The method of claim 3, wherein the shared beam forming element comprises an optical lens.

6. The method of claim 1, further comprising focusing the illumination laser beam using an optical lens.

7. The method of claim 1, further comprising focusing the reflected laser energy using an optical lens.

8. An apparatus to make ultrasonic measurements comprising:
- a laser generation source;
- an ultrasound source to generate ultrasonic surface displacements in a remote target;
- an illumination laser source to generate an illumination laser beam;
- at least one optical fiber to direct the illumination laser beam to the surface of the remote target where ultrasonic surface displacements at the remote target scatter the illumination laser beam to produce phase modulated light;
- at least one optical fiber to collect the phase-modulated light wherein a field of view of the at least one optical fiber to direct the illumination laser beam and the at least one optical fiber to collect phase modulated light substantially overlap;
- a processor to demodulate the phase-modulated light to obtain data representative of the ultrasonic surface displacements at the surface and render the ultrasonic measurements on the remote target based on the data representative of the ultrasonic surface displacements; and
- at least one optical fiber is terminated by an angled or curved surface designed to maximize the overlap of the fields of view of the fibers.

9. The apparatus of claim 8, wherein the ultrasound source comprises a generation laser source to generate a generation laser beam.

10. The apparatus of claim 9, further comprising at least one angle-terminated optical fiber to direct the generation laser beam to the surface of the remote target in order to generate ultrasonic surface displacements at a surface of the remote target.

11. The apparatus of claim 10, further comprising a shared beam forming element to focus the illumination laser beam, generation laser beam and phase modulated light.

* * * * *

UNITED STATES PATENT AND TRADEMARK OFFICE
CERTIFICATE OF CORRECTION

PATENT NO. : 7,576,848 B2 Page 1 of 1
APPLICATION NO. : 11/018994
DATED : August 18, 2009
INVENTOR(S) : Dubois et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 666 days.

Signed and Sealed this

Seventh Day of September, 2010

David J. Kappos
*Director of the United States Patent and Trademark Office*